(12) United States Patent
Li et al.

(10) Patent No.: US 11,927,511 B2
(45) Date of Patent: Mar. 12, 2024

(54) METHOD FOR STATISTICAL DISTRIBUTION CHARACTERIZATION OF DENDRITIC STRUCTURES IN ORIGINAL POSITION OF SINGLE CRYSTAL SUPERALLOY

(71) Applicants: NCS TESTING TECHNOLOGY CO., LTD, Beijing (CN); CENTRAL IRON AND STEEL RESEARCH INSTITUTE, Beijing (CN)

(72) Inventors: Dongling Li, Beijing (CN); Lei Zhao, Beijing (CN); Haizhou Wang, Beijing (CN); Xuejing Shen, Beijing (CN); Qingqing Zhou, Beijing (CN); Weihao Wan, Beijing (CN); Haozhou Feng, Beijing (CN)

(73) Assignees: NCS TESTING TECHNOLOGY CO., LTD, Beijing (CN); CENTRAL IRON AND STEEL RESEARCH INSTITUTE, Beijing (CN)

( * ) Notice: Subject to any disclaimer, the term of this patent is extended or adjusted under 35 U.S.C. 154(b) by 276 days.

(21) Appl. No.: 17/586,729

(22) Filed: Jan. 27, 2022

(65) Prior Publication Data
US 2022/0252488 A1    Aug. 11, 2022

(30) Foreign Application Priority Data
Feb. 6, 2021 (CN) .......................... 202110165083.X (51) Int. Cl.
*G01N 1/28* (2006.01)
*G01N 23/223* (2006.01)
*G01N 33/204* (2019.01)

(52) U.S. Cl.
CPC ........... *G01N 1/286* (2013.01); *G01N 23/223* (2013.01); *G01N 33/204* (2019.01); *G01N 2001/2866* (2013.01); *G01N 2001/2893* (2013.01)

(58) Field of Classification Search
CPC ................. G01N 1/286; G01N 23/223; G01N 2001/2866; G01N 2001/2893; G06F 17/10
See application file for complete search history.

(56) References Cited

U.S. PATENT DOCUMENTS
2022/0299455 A1* 9/2022 Li ...................... G01N 33/2028

OTHER PUBLICATIONS

Acer et al., "Effect of Growth Rate on the Microstructure and Microhardness in a Directionally Solidified Al—Zn—Mg Alloy", Metallurgical and Materials Transactions A, vol. 47A, Jun. 2016, p. 3040-3051. (Year: 2016).*

(Continued)

*Primary Examiner* — David P Porta
*Assistant Examiner* — Casey Bryant (57) ABSTRACT

The present application relates to a method for statistical distribution characterization of dendritic structures in original position of single crystal superalloy, and relates to the technical field of analysis of metal material composition and microstructure, comprising the following steps: step 1, processing a to-be-tested sample and determining a calibration coefficient; step 2, obtaining a two-dimensional element content distribution map of the to-be-tested sample; and step 3, determining the number and average spacing of primary dendrites. A composition distribution region analyzed in the present application is larger than the area of a distribution region of the traditional microscopic analysis method, and the sample preparation is simple. The distribution, number and average spacing of the primary dendrites can be obtained without metallographic corrosion sampling. There- (Continued)

fore, the present invention has the advantages of large statistical field of view, high efficiency and complete information, and the statistical data is more accurate and reliable.

8 Claims, 4 Drawing Sheets

(56) References Cited

OTHER PUBLICATIONS

Dong-ling et al. "Characterization of the elemental distribution of superalloy composite powders by micro beam X-ray fluorescence and laser-Induced breakdown spectroscopy", Spectrochimica Acta Part B, 169(2020) p. 1-13. (Year: 2020).*

Sudbrack et al. "Effect of Surface Preparation on the 815° C. Oxidation of Single-Crystal Nickel-Based Superalloys", JOM, vol. 67, No. 11, 2015, p. 2589-2598. (Year: 2015).*

* cited by examiner

METHOD FOR STATISTICAL DISTRIBUTION CHARACTERIZATION OF DENDRITIC STRUCTURES IN ORIGINAL POSITION OF SINGLE CRYSTAL SUPERALLOY

TECHNICAL FIELD

The present application relates to the technical field of analysis of metal material composition and microstructure, and particularly relates to a method for statistical distribution characterization of composition, number and average spacing of dendritic structures in original position of single crystal superalloy.

BACKGROUND

Directionally solidified nickel-based single crystal superalloy has excellent high-temperature strength, fatigue resistance, fracture toughness, and good oxidation and thermal corrosion resistance, and is the preferred material for turbine blades of aero-engines. The solidification structures are usually dendritic structures during directional solidification preparation of single crystal superalloy. The dendritic structure is a characteristic structure generated from the process of directional solidification of metallic material and is mainly formed by element segregation at a solid-liquid interface during non-equilibrium solidification of alloy, which is closely related to the solidification technology. Especially for nickel-base single crystal superalloy which is a preferred material for the turbine blade of an aero-engine, the main structure is a cross dendritic structure, and the characteristic parameters directly affect the thermo-mechanical properties and heat treatment technology of the alloy. The characteristic parameter that represents the dendritic structure is dendrite spacing, which has a decisive influence on the properties of the material. The spacing of primary dendrites is an important structure parameter of single crystal superalloy. Decrease of the spacing of the primary dendrites of the alloy can play a role of optimizing the as-cast structure of the alloy, effectively reduce the number of eutectic structure and the size of $\gamma'$ phase in the as-cast alloy, and optimize the morphology of carbide, thereby improving the fatigue life and durability of the superalloy.

During the solidification of the single crystal superalloy, solute redistribution leads to dendrite segregation of alloy elements. There are some elements such as Re (rhenium), W (tungsten) and Mo (molybdenum) in the dendrite stem, while many elements such as Al (aluminum), Hf (hafnium) and Ta (tantalum) exist in the inter-dendrites. Therefore, the distribution of the elements is closely related to the distribution of the dendritic structures. In addition, modern experimental studies show that there are acceptable ranges of dendrite spacing and cellular spacing under certain solidification conditions. The specific spacing is related to the solidification history within the ranges. It is necessary to further study the distribution of the dendrite spacing in order to investigate the stability and the reliability of the solidification technology. Therefore, the composition and distribution characterization of the dendritic structures are of great significance to improve the preparation technology of the single crystal superalloy and improve the mechanical properties of the material.

The cross of the dendritic structure of the single crystal superalloy is the dendrite. The width of the primary dendrite is usually 50-100 microns, and the distance between adjacent dendrites is more than 200 microns. Therefore, for the characterization method of the composition distribution, a good spatial resolution is required. At present, the traditional characterization methods of microstructure composition distribution are scanning electron microscope t combined with energy spectrum analysis and electron probe micro-analysis methods. The field of view for observation in these methods is limited, and the distribution of each element on local dendritic structures can be obtained so that quantitative accuracy needs to be improved. At present, the number of the dendritic structures and the spacing of the primary dendrites are measured mainly by direct metallographic method. The dendritic structures are displayed by a metallographic corrosion method, and then observed by a metallographic microscope and manually identified and counted. The method has the disadvantages of low efficiency and difficulty to control the corrosion degree. Uneven corrosion will occur in larger sections, thereby leading to incomplete corrosion or no display of some dendritic structures. In addition, the observation region in a single field of view in the metallographic method is limited, and the observation of the structures in the single field of view or local multiple fields of view cannot reflect the distribution characteristics of the overall microstructure of the material. Therefore, in general, the traditional methods for characterization of composition and average spacing of the dendritic structures have the problems of less information and inaccurate quantification, and cannot satisfy the needs of material workers to investigate the solidification technology and improve the properties of the material.

SUMMARY

With respect to the problems of less information and inaccurate quantification in the traditional characterization method of composition and average spacing of dendritic structures, the present application provides a method for statistical distribution characterization of composition, number and average spacing of dendritic structures in original position of single crystal superalloy.

The method for statistical distribution characterization of dendritic structures in original position of single crystal superalloy provided by the present application adopts the following technical solution:

A method for statistical distribution characterization of dendritic structures in original position of single crystal superalloy comprises the following steps:

step 1, processing a to-be-tested sample and determining a calibration coefficient;

grinding and polishing a (001) surface of directionally solidified single crystal superalloy containing characteristic elements to obtain the to-be-tested sample, wherein the content distribution of the characteristic elements in the dendritic structures and inter-dendritic structures is different;

conducting homogenization heat treatment on a directionally solidified single crystal superalloy block to obtain a calibration sample, wherein the calibration sample and the to-be-tested sample have the same composition and structure;

detecting the calibration sample by inductively coupled plasma atomic emitted spectroscopy to obtain the element content of the calibration sample from a chemical method;

grinding and polishing the surface of the calibration sample, conducting surface scanning on the calibration sample by a microbeam X-ray fluorescence spectrometry, and analyzing the scanning results to obtain the element content from a microbeam fluorescence method;

obtaining the calibration coefficient by dividing the element content from chemical method by the element content from the microbeam fluorescence method;

step 2, obtaining a two-dimensional elemental content distribution map of the to-be-tested sample;

conducting surface scanning on the to-be-tested sample by the microbeam X-ray fluorescence spectrometry to obtain a fluorescence intensity data matrix, and converting the fluorescence intensity data matrix into an initial element content data matrix, wherein the conditions for the microbeam X-ray fluorescence spectrometry are the same as those in step 1;

obtaining a calibration element content data matrix according to the following formula:

$$C=C_0*K$$

wherein C is the calibration element content data matrix, $C_0$ is the initial element content data matrix, and K is the calibration coefficient; and the calibration matrix is graphically transformed to obtain the two-dimensional content distribution map of each element;

step 3, determining the number and average spacing of primary dendrites.

Optionally, in step 1, the surface roughness Ra of the to-be-tested single crystal superalloy after surface grinding or polishing is not greater than 0.2 μm.

Optionally, the characteristic elements are at least one of Re, W, Ta and Ni.

Optionally, in step 1, when the calibration sample is determined by the microbeam X-ray fluorescence spectrometry, the instrument parameters of tube voltage, current and acquisition time of a fluorescence spectrometer are set according to the element content of the calibration sample to ensure that each element of the calibration sample generates sufficient fluorescence counting intensity; a high-precision sample moving platform is matched with a CCD camera and a 100× magnification lens to observe the position of a platform of the calibration sample and the analysis region of the calibration sample; and the surface of the calibration sample is determined by area analysis mode.

Optionally, the fluorescence intensity data matrix in step 2 is graphically transformed to obtain the two-dimensional intensity distribution map of each element; in step 3, the two-dimensional intensity distribution map of the characteristic element is marked; the number of primary dendrites is counted; and the average spacing of the primary dendrites is obtained according to the following formula:

$$\lambda=(S/N)^{0.5}$$

wherein S is the area of the field of view, and N is the number of the primary dendrites in the field of view.

Optionally, in step 3, the two-dimensional element content distribution map of the characteristic elements is marked; the number of the primary dendrites is counted; and the average spacing of the primary dendrites is obtained according to the following formula:

$$\lambda=(S/N)^{0.5}$$

wherein S is the area of the field of view, and N is the number of the primary dendrites in the field of view.

Optionally, the dendritic structures are automatically counted, partitioned and analyzed in combination with image processing software; a concentration threshold is preset for the two-dimensional element content distribution map of a characteristic element so that the characteristic elements with the content above the concentration threshold are highlighted, to obtain the changed two-dimensional content distribution map; the changed two-dimensional distribution content map is binarized to obtain a binarized image; and the binarized image is partitioned and analyzed to obtain the number and the average spacing of the primary dendrites in different regions of the dendritic structures.

Optionally, in step 3, a calculation formula of the calibration coefficient for calibration of scanning data is $C=C_0*K$, wherein $C_0$ is initial uncalibrated data, K is the calibration coefficient, and C is the calibrated data.

Optionally, in step 1, the calibration matrix is counted to obtain average content and standard deviation of the characteristic elements; and the concentration threshold in step 3 is set as the sum of the average content and the standard deviation of the characteristic elements.

The present application has at least one of the following beneficial technical effects:

1. At present, the composition distribution of the dendritic structures is determined by scanning electron microscopy combined with energy dispersive spectroscopy and an electron probe micro-analysis method (EPMA). The observation field of view is limited, and the observation surface and electrical conductivity of the samples are highly required. The microbeam X-ray fluorescence spectroscopy technology used in this method excites the surface of the sample with high-luminance X-ray obtained by multichannel capillary focusing technique, and the depth acting on material surface is much greater than that of the scanning electron microscope and eEPMA. Therefore, the requirement for the roughness of the surface is not high, and the conductivity of the sample is not strictly required, which is suitable for the analysis of various forms of samples. Therefore, there is no need for metallographic sample preparation on the to-be-tested surface, and the surface with satisfactory roughness can be ground by a grinder. At the same time, the matching of the high-precision sample platform and microscopic amplification equipment can realize the surface distribution analysis of large-region samples and accurate positioning of small region.

2. In this method, the positions, the number and the average spacing of the dendritic structures are determined according to the two-dimensional content distribution map the characteristic elements based on elemental segregation characteristics of materials in the dendritic structures. Compared with the traditional metallographic method, the sample preparation is simpler, and the distribution of the dendritic structures can be obtained without metallographic corrosion on the sample surface. Due to complex conditions when the metallographic method is used for corrosion by chemical reagents, the corrosion degree of the sample surface is uneven, leading to incomplete dendritic structures displayed and difficult identification. In addition, the limitations of uneven gray level and difficult multi-field splicing in metallographic image collection are overcome. The quantitative statistical information of composition distribution and dendritic structure distribution can be obtained in one analysis, which greatly improves the detection efficiency.

3. The existing metallographic image method is mainly image analysis for a single field of view, and the observed area of the field of view and the number of the dendritic structures are limited. The present invention can obtain the composition distribution characteristic map of the dendritic structures in the full field of view in a larger region of the material through large-range microbeam X-ray fluorescence spectral area scanning analysis, so that the phenomenon of incomplete statistics of dendritic structures at the edge during observation of single field of view is greatly eliminated. Therefore, the present invention has the advantages of large statistical field of view, high efficiency and full information, and the statistical data are more accurate and reliable.

DETAILED DESCRIPTION

The present application is further described below in detail in combination with the drawings.

Embodiments of the present application disclose a method for statistical distribution characterization of dendritic structures in original position of single crystal superalloy. The method comprises the following steps.

Step 1: Processing a to-be-Tested Sample and Determining a Calibration Coefficient.

Grinding or polishing a (001) surface of directionally solidified single crystal superalloy containing characteristic elements so that the surface roughness Ra after processing is not greater than 0.2 μm, to obtain the to-be-tested sample, wherein the characteristic elements are at least one of Re, W, Ta and Ni, and the content distribution of the characteristic elements in the dendritic structures and inter-dendritic structures is different.

Conducting homogenization heat treatment on a calibration directionally solidified single crystal superalloy block body to obtain a calibration sample, wherein the calibration sample and the to-be-tested sample have the same composition and structure;
  detecting the calibration sample by inductively coupled plasma spectroscopy to obtain the element content of the calibration sample from a chemical method;
  grinding and polishing the surface of the calibration sample; conducting surface scanning on the calibration sample by a microbeam X-ray fluorescence spectrometry; setting the instrument parameters of tube voltage, current and acquisition time of a fluorescence spectrometer according to the element content of the calibration sample to ensure that each element of the calibration sample generates sufficient fluorescence counting intensity; matching a high-precision sample moving platform with a CCD camera and a 100× magnification lens to observe the position of a platform of the sample and the analysis region of the sample; and determining the surface of the calibration sample by area analysis mode to obtain the element content by a microbeam fluorescence method.

Obtaining the calibration coefficient by dividing the element content from the chemical method by the element content from the microbeam fluorescence method.

Step 2: Obtaining a Two-Dimensional Element Content Distribution Map of the to-be-Tested Sample.

Conducting surface scanning on the to-be-tested sample by the microbeam X-ray fluorescence spectrometry to obtain a fluorescence intensity data matrix, and graphically transforming the fluorescence intensity data matrix to obtain the two-dimensional element content distribution map of each element; converting the fluorescence intensity into an initial element content by a quantitative method of an instrument to obtain an initial element content data matrix, wherein the conditions for the microbeam X-ray fluorescence spectrometry are the same as those in step 1;
  obtaining a calibration element content data matrix according to the following formula:

$$C = C_0 * K$$

wherein C is the calibration element content data matrix, $C_0$ is the initial element content data matrix, and K is the calibration coefficient. The calibration element content data matrix is graphically transformed to obtain the two-dimensional element content distribution map of each element; and then, the calibration element content data matrix is counted to obtain the average content and the standard deviation of each element on the whole analysis surface.

Step 3: Determining the Number and Average Spacing of Primary Dendrites.

The primary dendrites are marked in the two-dimensional element content distribution map of the characteristic elements or in the two-dimensional element intensity distribution map; then, the number of the primary dendrites is counted; and the total average spacing is calculated according to the area of the total field of view and the number of the primary dendrites. The calculation formula is:

$$\lambda = (S/N)^{0.5}$$

wherein S is the area of the field of view, and N is the number of the primary dendrites in the field of view.

The dendritic structures are automatically counted, partitioned and analyzed in combination with image processing software. A concentration threshold is set for the two-dimensional content distribution map of the characteristic element obtained in step 2 so that the characteristic elements with the content above the concentration threshold on the primary dendrites are highlighted, to obtain the changed two-dimensional element content distribution map; and the concentration threshold can be set as the sum of the average content and the standard deviation of the characteristic elements. The two-dimensional distribution map of the element content is processed by universal image processing software; the changed two-dimensional element content distribution map is binarized to remove abnormal scratches and debris to obtain a binarized image; the number of the primary dendrites on the binarized image is counted; the position of each primary dendrite is recorded; at the same time, the binarized image is partitioned and analyzed; and the average spacing of the dendrites in different regions is calculated to obtain the number and the average spacing of the primary dendrites in different regions of the dendritic structures.

Embodiments

Step 1: Processing a to-be-Tested Sample and Determining a Calibration Coefficient.

Single crystal superalloy with crystal orientation (001) and diameter of 15 mm is prepared through spiral crystal selection by selecting nickel base master alloy containing characteristic elements and processing the alloy by a directional solidification technology. The characteristic elements are elements with content larger than 1% and obvious dendritic segregation in the single crystal superalloy, and the characteristic elements may be at least one of Re, W, Ta and Ni. The single crystal superalloy (001) surface is subjected to finish machining of grinding or polishing by a grinder to obtain the to-be-tested sample. The to-be-tested sample has a smooth surface and surface roughness Ra not greater than 0.2 μm.

The alloy with the same composition and structure as the to-be-tested sample is selected. The alloy has a diameter of 20 mm and a height of 20 mm. The sample is subjected to homogenization heat treatment as the calibration sample for quantitative analysis of the composition of the alloy.

A 10 mm calibration sample is cut along the height direction, and crumb samples are drilled from different parts of the cross section of the calibration sample and uniformly merged. The contents of elements Cr, Mo, Al, Co, Re, Ta and W in the crumb samples are determined by inductively coupled plasma spectroscopy to obtain the content of each element of the calibration sample from a chemical method, as shown in Table 1.

TABLE 1

Element content of calibration sample from chemical method

| Element | Cr | Mo | Al | Co | Re | Ta | W | Ni |
|---------|------|------|------|------|------|------|------|---------|
| Content | 4.99 | 2.57 | 5.91 | 8.07 | 2.51 | 5.00 | 4.63 | Balance |

The cut section of another reserved calibration sample is ground or polished, and the section is scanned and analyzed by microbeam X-ray fluorescence spectrometry.

The instrument parameters of tube voltage, current and acquisition time of a fluorescence spectrometer are set according to the element content of the calibration sample to ensure that each element of the calibration sample generates sufficient fluorescence counting intensity. A selected X-ray tube has voltage of 50 KV, current of 180 μA and single pixel acquisition time of 100 ms. A high-precision sample moving platform is matched with a CCD camera and a 100× magnification lens to observe the position of a platform of the calibration sample and the analysis region of the calibration sample; and the section of the calibration sample is determined by area analysis mode. The area of the scanning region is set as 6 mm×6 mm. The data obtained by scanning is a data matrix representing the fluorescence intensity count of each pixel point. The data matrix is processed by computer software to obtain the content of each element of the calibrated sample from a microbeam fluorescence method, as shown in Table 2.

TABLE 2

Element content (wt %) of calibration sample from microbeam fluorescence method

| Element | Cr | Mo | Al | Co | Re | Ta | W | Ni |
|---------|------|------|------|------|------|------|------|---------|
| Content | 4.30 | 2.47 | 3.79 | 7.83 | 1.99 | 5.10 | 3.67 | Balance |

The quantitative calibration coefficients of the element are obtained by dividing the element content from the chemical method through the inductively coupled plasma spectroscopy by the element content from the microbeam fluorescence method through the microbeam X-ray fluorescence spectrometry, as shown in Table 3. The calibration coefficient is saved as a new quantitative method for the material.

TABLE 3

Calibration coefficients of elements

| Element | Cr | Mo | Al | Co | Re | Ta | W |
|---------|------|------|------|------|------|------|------|
| Calibration coefficient | 1.16 | 1.04 | 1.56 | 1.03 | 1.26 | 0.98 | 1.26 |

Step 2: Obtaining a Two-Dimensional Element Content Distribution Map of the to-be-Tested Sample.

Figure 1:
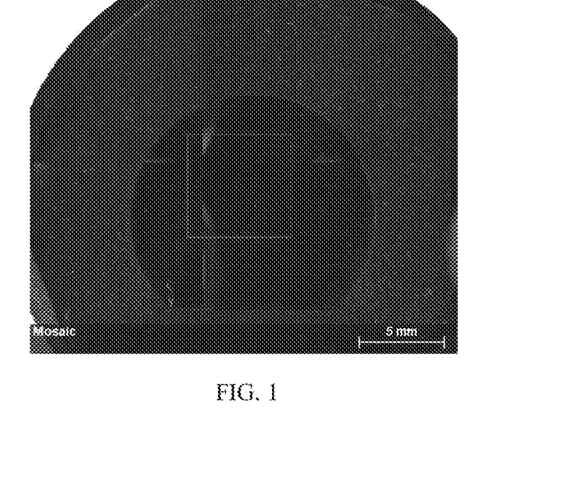
FIG. 1 is an analysis region of microbeam X-ray fluorescence spectrometry to be tested.

The surface of the to-be-tested sample is scanned and analyzed by the microbeam X-ray fluorescence spectrometry under the same instrument conditions as those in step 1. The area of the scanning region is set as 6 mm×6 mm. The scanning range is shown in FIG. 1. A fluorescence intensity data matrix is obtained, and is graphically transformed to obtain the two-dimensional intensity distribution map of each element. The fluorescence intensity is converted into an initial element content by a quantitative method of an instrument to obtain an initial element content data matrix; and then the initial element content data matrix is calibrated quantitatively by the calibration coefficient. The calculation formula is shown in formula (1).

$$C = C_0 * K \quad (1)$$

wherein C is the calibration element content data matrix, $C_0$ is the initial element content data matrix, and K is the calibration coefficient.

The calibrated data C is converted into graphs by computer software of matlab and origin to obtain the two-dimensional element content distribution map of each element. At the same time, the average content and the standard deviation of element content are obtained from the calibrated data by a statistical method. The average content of each element is shown in Table 4.

TABLE 4

Average element content (wt %) of to-be-tested sample

| Element | Cr | Mo | Ta | W | Re | Al | Co |
|---------|------|------|------|------|------|------|------|
| Average content | 5.86 | 2.37 | 5.56 | 4.15 | 2.34 | 5.33 | 7.73 |

The dendritic structure distribution displayed on the two-dimensional element intensity distribution map and on the two-dimensional element content distribution map is consistent.

Figure 2:
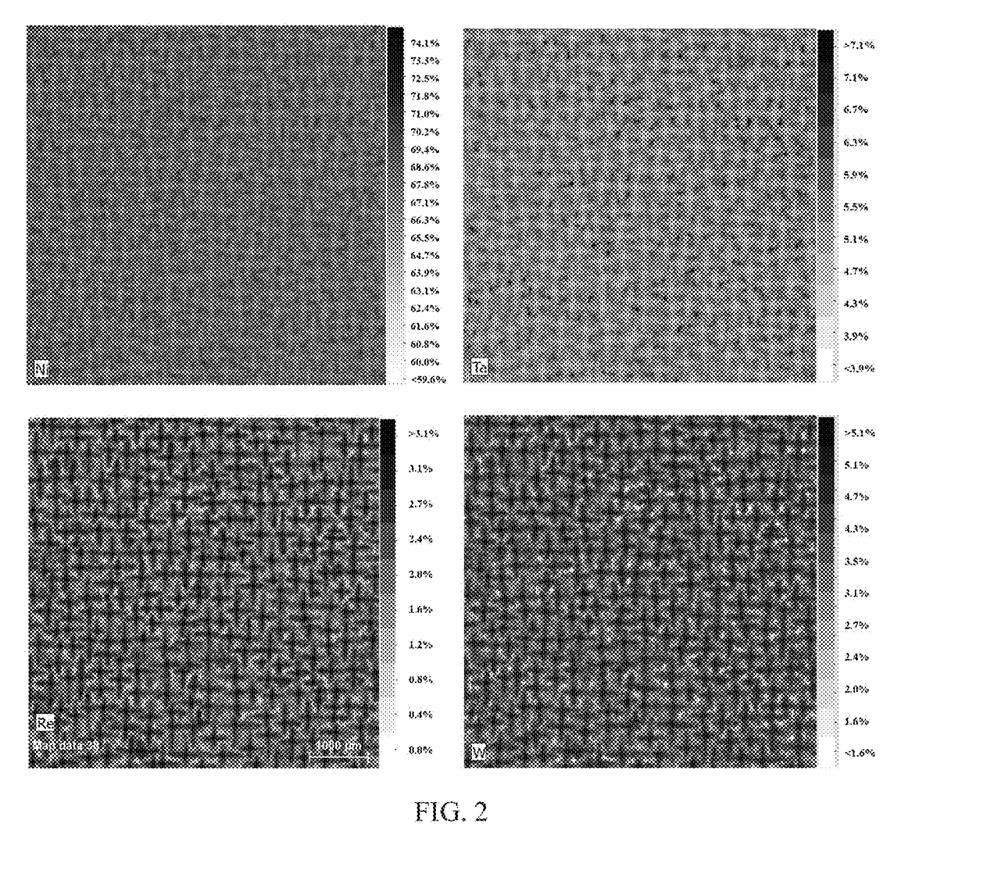
FIG. 2 is a two-dimensional content distribution map of Ni, Ta, Re and W.

The microbeam X-ray fluorescence spectrometry has good detection ability for high content of characteristic elements and can achieve good presentation of dendritic segregation of the characteristic elements. The two-dimensional element content distribution map of Ni, Ta, Re and W is shown in FIG. 2, which indicates that the content distribution of the above four characteristic elements in dendrites and between dendrites is obviously different. The elements Re and W have positive segregation in primary dendrites, and have content significantly higher than that in interdendritic structures, while the distribution of elements Ni and Ta is opposite.

Step 3: Determining the Number and Average Spacing of Primary Dendrites.

For single crystal superalloy, four characteristic elements of Ni, Ta, Re and W can exhibit the distribution of the dendritic structures. The position of maximum positive segregation of Re and W is in the center of primary dendrites. Therefore, the center position of the primary dendrites can be marked on the two-dimensional element intensity distribution map or the two-dimensional element content distribution map directly according to the distribution characteristics of element Re or W.

Figure 3:
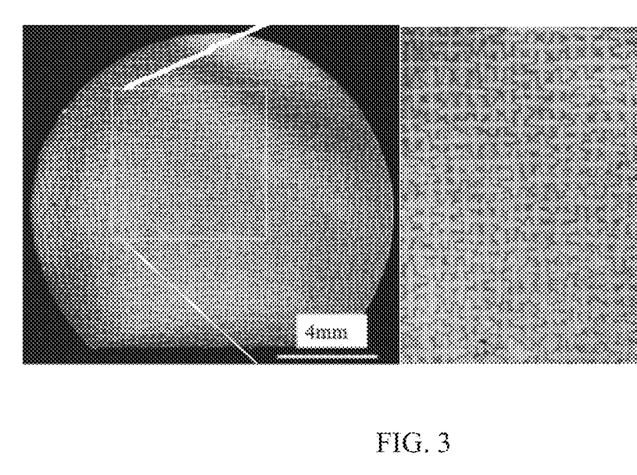
FIG. 3 is a two-dimensional distribution content map of labeled element Re.

By taking element Re as an example, the center of the primary dendrites of the dendritic structures is marked according to the two-dimensional distribution map of Re element content obtained in step 2, as shown in FIG. 3. The number of the primary dendrites is counted, and then the average spacing of the primary dendrites is calculated. The calculation formula is shown in formula (2):

$$\lambda = (S/N)^{0.5} \qquad (2)$$

wherein $\lambda$ is the average spacing of the primary dendrites, S is the area of the field of view, and N is the number of the primary dendrites in the field of view.

The area of the field of view in a white dotted line frame in FIG. 3 is 9 mm$^2$. The number of the primary dendrites is counted as 73, and the number of the dendrites with edge segmentation is 6, based on a weight of 0.5. Thus, the number of the primary dendrites is 70. According to the formula (2), the average spacing of the primary dendrites in the white frame is 358 sm.

Figure 4:
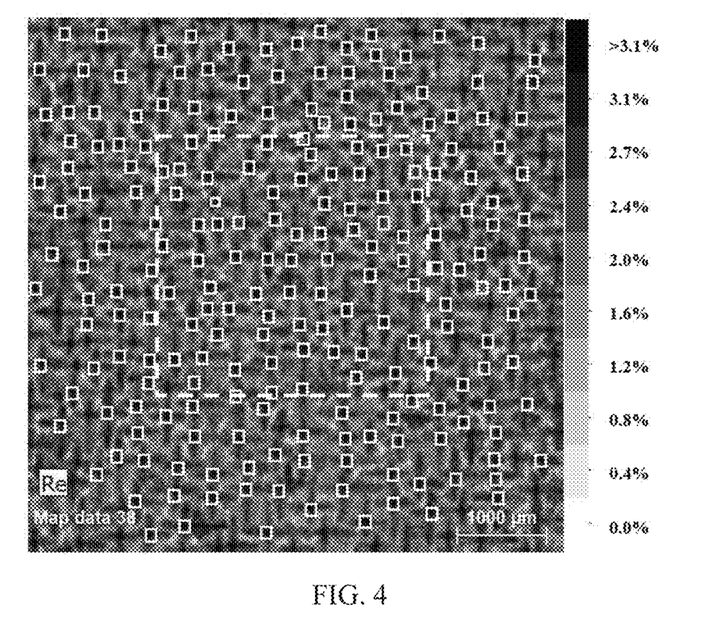
FIG. 4 is a secondary two-dimensional distribution content map of element Re.

The dendritic structures can also be automatically counted, partitioned and analyzed in combination with image processing software. Firstly, a concentration threshold is set for the two-dimensional distribution content map of the characteristic element so that the elements with high concentration on the primary dendrites are highlighted, to obtain the changed two-dimensional distribution map of content. The concentration threshold can be set as the sum of the average content and the standard deviation. By taking element Re as an example, the statistical results of calibrated data of element Re are shown in Table 5, and the concentration threshold of Re is calculated as 2.82%. The element distribution information below the threshold is replaced by the same white color, and the changed two-dimensional content distribution map is shown in FIG. 4. It can be known that elements Re with content higher than 2.82% are basically distributed on the primary dendrites.

Figure 5:
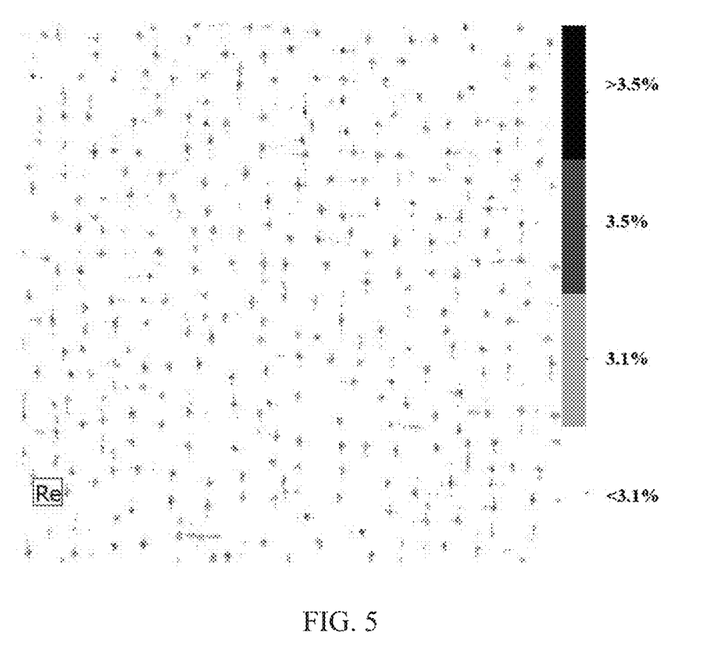
FIG. 5 is a binarized image of element Re.

Then, the changed two-dimensional content distribution map of elements Re is imported into general image processing software such as Image J. The image is binarized, and abnormal scratches and debris are removed to obtain a binarized image, as shown in FIG. 5.

Because the distribution of elements Ni and Ta is opposite to that of elements Re and W, the two-dimensional element content distribution map of elements Ni and Ta should be inverted at first to make the center brightness of the cross dendrite the lowest. Then, the above process is adopted for processing to obtain the binarized image.

The image processing software is used to automatically count the number of the binarized images and record the position of each primary dendrite, as shown in Table 6. The number of the primary dendrites obtained by automatic statistics is 285. The average spacing of the primary dendrites in a region of 6 mm*6 mm is calculated according to the formula (1) is 355 μm.

Figure 6:
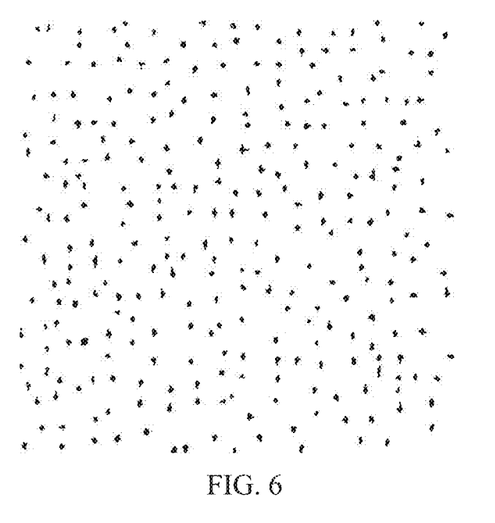
FIG. 6 is a region segmentation map of a binarized image.

At the same time, the binarized images can be segmented into 9 small regions of 2 mm-2 mm, as shown in FIG. 6. The number of the primary dendrites in different regions is counted, and the average spacing of the dendrites in different regions is calculated according to the regional area to obtain the number and the average spacing of the primary dendrites in different regions of the dendritic structures, as shown in Table 7.

TABLE 5

Statistical results of data analysis of Re element after calibration

| data point | Average value | Standard deviation | Minimum value | Maximum value | Median |
|---|---|---|---|---|---|
| 360000 | 2.344% | 0.473% | 0.345% | 4.042% | 2.346% |

TABLE 6

Positions of centers in different primary dendrites

| Characteristic | X(mm) | Y(mm) | Characteristic | X(mm) | Y(mm) | Characteristic | X(mm) | Y(mm) |
|---|---|---|---|---|---|---|---|---|
| 1 | 0.026 | 1.652 | 150 | 2.976 | 0.035 | 275 | 5.689 | 5.264 |
| 2 | 0.025 | 1.205 | 151 | 3.094 | 4.201 | 276 | 5.699 | 0.695 |
| 3 | 0.070 | 0.102 | 152 | 3.077 | 1.060 | 977 | 5.703 | 0.356 |
| 4 | 0.081 | 2.958 | 153 | 3.076 | 1.846 | 278 | 5.773 | 1.032 |
| 5 | 0.079 | 4.398 | 154 | 3.078 | 2.534 | 279 | 5.777 | 4.452 |
| 6 | 0.124 | 5.408 | 155 | 3.096 | 2.294 | 280 | 5.866 | 2.488 |
| 7 | 0.119 | 4.164 | 156 | 3.093 | 1.340 | 281 | 5.887 | 5.782 |
| 8 | 0.124 | 0.931 | 157 | 3.126 | 4.692 | 282 | 5.910 | 2.221 |
| 9 | 0.178 | 2.114 | 158 | 3.158 | 4.537 | 283 | 5.915 | 4.185 |
| 10 | 0.200 | 4.925 | 159 | 3.158 | 5.019 | 284 | 5.951 | 3.286 |
| ... | ... | ... | ... | ... | ... | 285 | 5.965 | 1.339 |

TABLE 7

Number and average spacing of primary dendrites in different regions

| Region | 1 | 2 | 3 | 4 | 5 | 6 | 7 | 8 | 9 |
|---|---|---|---|---|---|---|---|---|---|
| Number | 33 | 34 | 31 | 34 | 33 | 30 | 32 | 29 | 29 |
| Average spacing (μm) | 348 | 343 | 359 | 343 | 348 | 365 | 354 | 371 | 371 |

Figure 7:
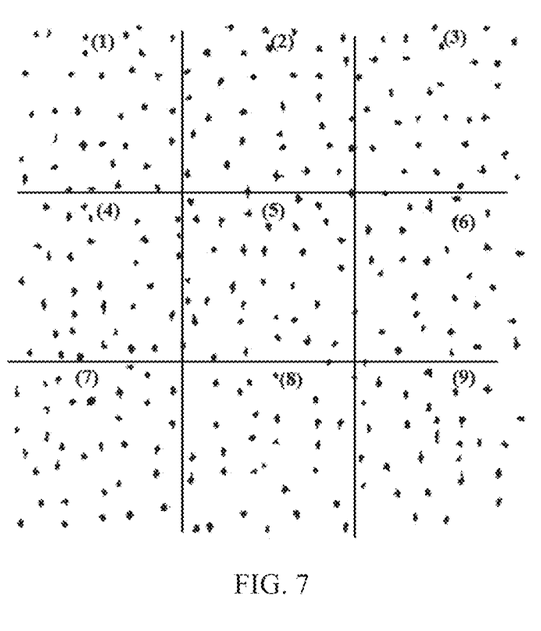
FIG. 7 is a metallograph of dendritic structures after metallographic corrosion.

For comparison, the surface scanning region of the to-be-tested sample is metallographically corroded with 10% copper sulfate (m/V)+50% hydrochloric acid (V/V)+10% sulfuric acid (V/V) aqueous solution. The metallograph of the dendritic structures after corrosion is shown in FIG. 7. It can be known that the two-dimensional element content distribution map of elements Ni, Ta, Re and W obtained by the microbeam X-ray fluorescence spectrometry is basically consistent with the metallograph of the dendritic structures obtained after metallographic corrosion, but the dendrite distribution in the two-dimensional distribution map of element content is more clear. In addition, partial corrosion may be uneven during metallographic corrosion, and the metallograph of the dendritic structures is formed by splicing a plurality of images of the field of view taken by an optical microscope, with certain background brightness differences. The gray differences between secondary dendrites and the primary dendrites are not obvious, so the automatic statistics of the image software cannot be realized. The metallograph of the dendritic structures needs to be manually identified and counted. The counted number of the dendrites is 277, and the calculated average spacing of the dendrites is 360 μm.

In the method, according to the element segregation characteristics of the dendritic structures of single crystal superalloy material, the positions, the number and the average spacing of the dendritic structures are determined through the two-dimensional element content distribution map of the characteristic elements. The quantitative statistical information of composition distribution and dendritic structure distribution can be obtained by one analysis. The method has the advantages of large field of view, high efficiency and complete information, and the statistical data is more accurate and reliable.

The above illustrates the preferred embodiments of the present application and is not intended to limit the protection scope of the present application. Therefore, any equivalent change made in accordance with the structure, shape and principle of the present application shall be covered within the protection scope of the present application.

What is claimed is:

1. A method for statistical distribution characterization of dendritic structures in original position of single crystal superalloy, comprising the following steps:
   step 1, processing a to-be-tested sample and determining a calibration coefficient;
   grinding and polishing a (001) surface of directionally solidified single crystal superalloy containing characteristic elements to obtain the to-be-tested sample, wherein the content distribution of the characteristic elements in the dendritic structures and inter-dendritic structures is different;
   conducting homogenization heat treatment on a directionally solidified single crystal superalloy block to obtain a calibration sample, wherein the calibration sample and the to-be-tested sample have the same composition and structure;
   detecting the calibration sample by inductively coupled plasma atomic emitted spectroscopy to obtain the element content of the calibration sample from a chemical method;
   grinding and polishing the surface of the calibration sample, conducting surface scanning on the calibration sample by a microbeam X-ray fluorescence spectrometry, and analyzing the scanning results to obtain the element content from a microbeam fluorescence method;
   obtaining the calibration coefficient by dividing the element content from the chemical method by the element content from the microbeam fluorescence method;
   step 2, obtaining a two-dimensional elemental content distribution map of the to-be-tested sample;
   conducting surface scanning on the to-be-tested sample by the microbeam X-ray fluorescence spectrometry to obtain a fluorescence intensity data matrix, and converting the fluorescence intensity data matrix into an initial element content data matrix, wherein the conditions for the microbeam X-ray fluorescence spectrometry are the same as those in step 1;
   obtaining a calibration element content data matrix according to the following formula:

$$C = C_0 * K$$

wherein C is the calibration element content data matrix, $C_0$ is the initial element content data matrix, and K is the calibration coefficient; and the calibration matrix is graphically transformed to obtain the two-dimensional content distribution map of each element;
   step 3, determining the number and average spacing of primary dendrites.

2. The method for statistical distribution characterization of dendritic structures in original position of single crystal superalloy according to claim 1, wherein in step 1, the surface roughness Ra of the to-be-tested single crystal superalloy after surface grinding or polishing is not greater than 0.2 μm.

3. The method for statistical distribution characterization of dendritic structures in original position of single crystal superalloy according to claim 1, wherein the characteristic elements are at least one of Re, W, Ta and Ni.

4. The method for statistical distribution characterization of dendritic structures in original position of single crystal superalloy according to claim 1, wherein in step 1, when the calibration sample is determined by the microbeam X-ray fluorescence spectrometry, the instrument parameters of tube voltage, current and acquisition time of a fluorescence spectrometer are set according to the element content of the calibration sample to ensure that each element of the calibration sample generates sufficient fluorescence counting intensity; a high-precision sample moving platform is matched with a CCD camera and a 100× magnification lens to observe the position of a platform of the calibration sample and the analysis region of the calibration sample; and the surface of the calibration sample is determined by area analysis mode.

5. The method for statistical distribution characterization of dendritic structures in original position of single crystal superalloy according to claim 1, wherein the fluorescence intensity data matrix in step 2 is graphically transformed to obtain the two-dimensional intensity distribution map of each element; in step 3, the two-dimensional intensity distribution map of the characteristic elements is marked; the number of primary dendrites is counted; and the average spacing of the primary dendrites is obtained according to the following formula:

$$\lambda = (S/N)^{0.5}$$

wherein S is the area of the field of view, and N is the number of the primary dendrites in the field of view.

6. The method for statistical distribution characterization of dendritic structures in original position of single crystal superalloy according to claim 1, wherein in step 3, the two-dimensional element content distribution map of the characteristic elements is marked; the number of the primary dendrites is counted; and the average spacing of the primary dendrites is obtained according to the following formula:

$$\lambda = (S/N)^{0.5}$$

wherein S is the area of the field of view, and N is the number of the primary dendrites in the field of view.

7. The method for statistical distribution characterization of dendritic structures in original position of single crystal superalloy according to claim 1, wherein the dendritic structures are automatically counted, partitioned and analyzed in combination with image processing software; a concentration threshold is preset for the two-dimensional element content distribution map of a characteristic element so that the characteristic elements with the content above the concentration threshold are highlighted, to obtain the changed two-dimensional content distribution map; the changed two-dimensional distribution content map is binarized to obtain a binarized image; and the binarized image is partitioned and analyzed to obtain the number and the average spacing of the primary dendrites in different regions of the dendritic structures.

8. The method for statistical distribution characterization of dendritic structures in original position of single crystal superalloy according to claim 7, wherein in step 1, the calibration matrix is counted to obtain average content and standard deviation of the characteristic elements; and the concentration threshold in step 3 is set as the sum of the average content and the standard deviation of the characteristic elements.

* * * * *